US00PP26956P2

(12) United States Plant Patent
Wood

(10) Patent No.: US PP26,956 P2
(45) Date of Patent: Jul. 19, 2016

(54) ***HYDRANGEA* PLANT NAMED 'SMNHPRZEP'**

(50) Latin Name: *Hydrangea paniculata*
Varietal Denomination: SMNHPRZEP

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 14/544,637

(22) Filed: Jan. 23, 2015

(51) Int. Cl.
*A01H 5/02* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Hydrangea* plant named 'SMNHPRZEP', characterized by its upright and somewhat outwardly spreading plant habit; strong and sturdy stems; freely flowering habit; showy inflorescences with sterile flowers that are initially white in color and becoming hot pink to red in color; and good garden performance.

2 Drawing Sheets

Botanical designation: *Hydrangea paniculata.*
Cultivar denomination: 'SMNHPRZEP'.

BACKGROUND OF THE INVENTION

The present invention relates to a new and distinct *Hydrangea* plant, botanically known as *Hydrangea paniculata* and hereinafter referred to by the name 'SMNHPRZEP'.

The new *Hydrangea* plant is a product of a planned breeding program conducted by the Inventor in Grand Haven, Mich. The objective of the breeding program was to develop new early-flowering *Hydrangea* plants with strong stems and large and attractive inflorescences.

The new *Hydrangea* plant originated from an open-pollination in July, 2004 of *Hydrangea paniculata* 'Little Lamb', disclosed in U.S. Plant Pat. No. 15,395, as the female, or seed parent and an unknown selection of *Hydrangea paniculata* as the male, or pollen, parent. The new *Hydrangea* plant was discovered and selected by the Inventor as a single flowering plant from within the progeny of the stated open-pollination in a controlled environment in Grand Haven, Mich. in July, 2009.

Asexual reproduction of the new *Hydrangea* plant by softwood cuttings in a controlled environment in Grand Haven, Mich. since June, 2010 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHPRZEP'. These characteristics in combination distinguish 'SMNHPRZEP' as a new and distinct *Hydrangea* plant:

1. Upright and somewhat outwardly spreading plant habit.
2. Strong and sturdy stems.
3. Freely flowering habit.
4. Showy inflorescences with sterile flowers that are initially white in color and becoming hot pink to red in color.
5. Good garden performance.

Plants of the new *Hydrangea* differ from plants of the female parent, 'Little Lamb', in the following characteristics:

1. Plants of the new *Hydrangea* are larger than plants of 'Little Lamb'.
2. Plants of the new *Hydrangea* have stronger stems than plants of 'Little Lamb'.
3. Plants of the new *Hydrangea* and 'Little Lamb' differ in sterile flower color as plants of 'Little Lamb' have pink-colored sterile flowers.

Plants of the new *Hydrangea* can be compared to plants of *Hydrangea paniculata* 'Limelight', disclosed in U.S. Plant Pat. No. 12,874. In side-by-side comparisons, plants of the new *Hydrangea* differed primarily from plants of 'Limelight' in the following characteristics:

1. Plants of the new *Hydrangea* were more compact than plants of 'Limelight'.
2. Plants of the new *Hydrangea* and 'Limelight' differed in sterile flower color as plants of 'Limelight' had light green-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMNHPRZEP' growing in an outdoor nursery.

The photograph on the second sheet is a close-up view of typical inflorescences of 'SMNHPRZEP'.

Plants used in the photographs were four years old.

DETAILED BOTANICAL DESCRIPTION

Plants used for the following description were grown during the summer in three-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the photographs and description were taken. Plants were overwintered in a polyethylene-covered greenhouse. In the following description, color references are made to The Royal Horticultural Society Colour Chart, 1995 Edition, except where general terms of ordinary dictionary significance are used.

Botanical description: *Hydrangea paniculata* 'SMNHPRZEP'.

Parentage:

*Female, or seed, parent.*—*Hydrangea paniculata* 'Little Lamb', disclosed in U.S. Plant Pat. No. 15,395.

*Male, or pollen, parent.*—Unknown selection of *Hydrangea paniculata*, not patented.

Propagation:

*Type cutting.*—By softwood cuttings.

*Time to initiate roots, summer.*—About 18 days at temperatures about 24° C.

*Time to produce a rooted young plant, summer.*—About three months at temperatures about 24° C.

*Root description.*—Medium in thickness; fibrous; creamy white to brown in color.

*Rooting habit.*—Freely branching; dense.

Plant description:

*Plant form and growth habit.*—Perennial deciduous shrub; upright and somewhat outwardly spreading plant habit; broad inverted triangle; strong and sturdy lateral branches; freely branching habit with about 29 lateral branches developing per plant; vigorous growth habit.

*Plant height.*—About 56.2 cm.

*Plant diameter or area of spread.*—About 78.2 cm.

*Lateral branches.*—Length: About 44 cm to 76 cm. Diameter: About 7 mm. Internode length: About 4.3 cm to 4.7 cm. Texture: Pubescent. Strength: Strong, sturdy. Aspect: About 35° to 45° from vertical. Color, developing: Close to 147C overlain with close to 176B. Color, developed: Close to 138B overlain with close to 199A.

Leaf description:

*Arrangement.*—Opposite, simple.

*Length.*—About 10 cm.

*Width.*—About 5.6 cm.

*Shape.*—Ovate.

*Apex.*—Acuminate.

*Base.*—Obtuse to cuneate.

*Margin.*—Serrulate; slightly undulate.

*Texture, upper surface.*—Smooth, glabrous.

*Texture, lower surface.*—Slightly pubescent.

*Venation pattern.*—Pinnate.

*Color.*—Developing leaves, upper surface: Close to 144A. Developing leaves, lower surface: Close to 146B. Fully expanded leaves, upper surface: Close to 137A tinged with close to 146C; venation, close to 146C. Fully expanded leaves, lower surface: Close to 138B; venation, close to 146D.

*Petioles.*—Length: About 1.3 cm. Diameter: About 3 mm. Texture, upper surface: Smooth, glabrous. Texture, lower surface: Slightly pubescent. Color, upper surface: Close to 147B. Color, lower surface: Close to 146C.

Inflorescence & flower description:

*Flower type and habit.*—Single sterile and fertile flowers arranged on large terminal panicles; flowers face upright and outwardly.

*Fragrance.*—None detected.

*Natural flowering season.*—Continuous flowering throughout the summer into the autumn Grand Haven, Mich.

*Quantity of flowers.*—Freely flowering habit; at least 100 fertile flowers and at least 100 sterile flowers develop per inflorescence.

*Inflorescence height.*—About 15 cm.

*Inflorescence diameter.*—About 17.7 cm.

*Flower diameter, fertile flowers.*—About 3 mm.

*Flower depth (height), fertile flowers.*—About 2 mm.

*Flower diameter, sterile flowers.*—About 3.5 cm.

*Flower depth (height), sterile flowers.*—About 2.5 cm.

*Flower buds, fertile flowers.*—Length: About 3 mm. Diameter: About 2.5 mm. Shape: Orbicular, lobed. Color: Close to 155A.

*Flower buds, sterile flowers.*—Length: About 1.2 mm. Diameter: About 1.2 mm. Shape: Orbicular, lobed. Color: Close to 155A.

*Petals, fertile flowers.*—Arrangement: Four in a single whorl. Length: About 1 mm. Width: About 1.25 mm. Shape: Ovate. Apex: Acute. Base: Obtuse. Margin: Entire. Texture, upper and lower surfaces: Smooth, glabrous. Color: When opening, upper surface: Close to 145D. When opening, lower surface: Close to 145C. Fully opened, upper surface: Close to 155C tinted with close to 145C; color does not change with development. Fully opened, lower surface: Close to 155C tinted with close to 145D; color does not change with development.

*Petals, sterile flowers.*—Arrangement: Four in a single whorl. Length: About 1.5 mm. Width: About 1 mm. Shape: Elliptic to ovate. Apex: Acute. Base: Rounded to slightly acute. Margin: Entire. Texture, upper and lower surfaces: Smooth, glabrous. Color: When opening, upper and lower surfaces: Close to 145C. Fully opened, upper surface: Close to 155C tinted with close to 145C; color does not change with development. Fully opened, lower surface: Close to 155C tinted with close to 145D; color does not change with development.

*Sepals, fertile flowers.*—Quantity per flower: Five in a single whorl. Length: About 1 mm. Width: About 2 mm. Shape: Fused. Apex: Acute. Base: Obtuse. Margin: Entire. Texture, upper and lower surfaces: Smooth, glabrous. Color: When opening, upper surface: Close to 145A. When opening, lower surface: Close to 145C. Fully opened, upper surface: Close to 145A. Fully opened, lower surface: Close to 145B.

*Sepals, sterile flowers*.—Quantity per flower: Four in a single whorl. Length: About 1.6 cm. Width: About 1.6 cm. Shape: Elliptical to obovate. Apex: Obtuse. Base: Obtuse to slightly acute. Margin: Entire. Texture, upper and lower surfaces: Smooth, glabrous. Color: When opening, upper and lower surfaces: Close to 145C. Fully opened, upper surface: Close to 155C overlain with close to 145C; color becoming closer to 67C and eventually close to 58A with development. Fully opened, lower surface: Close to 155C slightly shaded with close to 145D; color does not change with development.

*Pedicels, fertile flowers*.—Length: About 1 mm. Diameter: About 1 mm. Angle: About 5° to 90° from inflorescence axis. Strength: Strong, sturdy. Texture: Slightly pubescent. Color: Close to 145D.

*Pedicels, sterile flowers*.—Length: About 1.9 cm. Diameter: About 1.1 mm. Angle: Erect to about 45° from inflorescence axis. Strength: Strong, sturdy. Texture: Smooth, glabrous. Color: Close to 145D.

*Reproductive organs, fertile flowers*.—Stamens: Quantity per flower: About eight. Filament length: About 0.75 mm. Filament color: Close to 145A. Anther shape: Lanceolate. Anther length: About 1 mm. Anther color: Close to 145A. Pollen amount: None observed. Pistils: Pistil quantity per flower: One. Pistil length: About 1 mm. Stigma shape: Club-shaped. Stigma color: Close to 145A. Style length: About 0.75 mm. Style color: Close to 145A. Ovary color: Close to 155A and 145B.

*Reproductive organs, sterile flowers*.—Stamens: Quantity per flower: About eight to ten. Filament length: About 2.5 mm. Filament color: Close to 155C. Anther shape: Lobed. Anther length: About 1 mm. Anther color: Close to 162B. Pollen amount: Scarce. Pollen color: Close to 155B. Pistils: Pistil quantity per flower: One. Pistil length: About 1 mm. Stigma shape: Club-shaped. Stigma color: Close to 145A. Style length: About 0.75 mm. Style color: Close to 145A. Ovary color: Close to 155A and 145B.

*Seeds and fruits*.—Seed and fruit development has not been observed on plants of the new *Hydrangea*.

Disease & pest resistance: Plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind; to be resistant to sun scald; and to tolerate temperatures ranging from about −32° C. to about 36° C.

It is claimed:

1. A new and distinct *Hydrangea* plant named 'SMNHPRZEP' as illustrated and described.

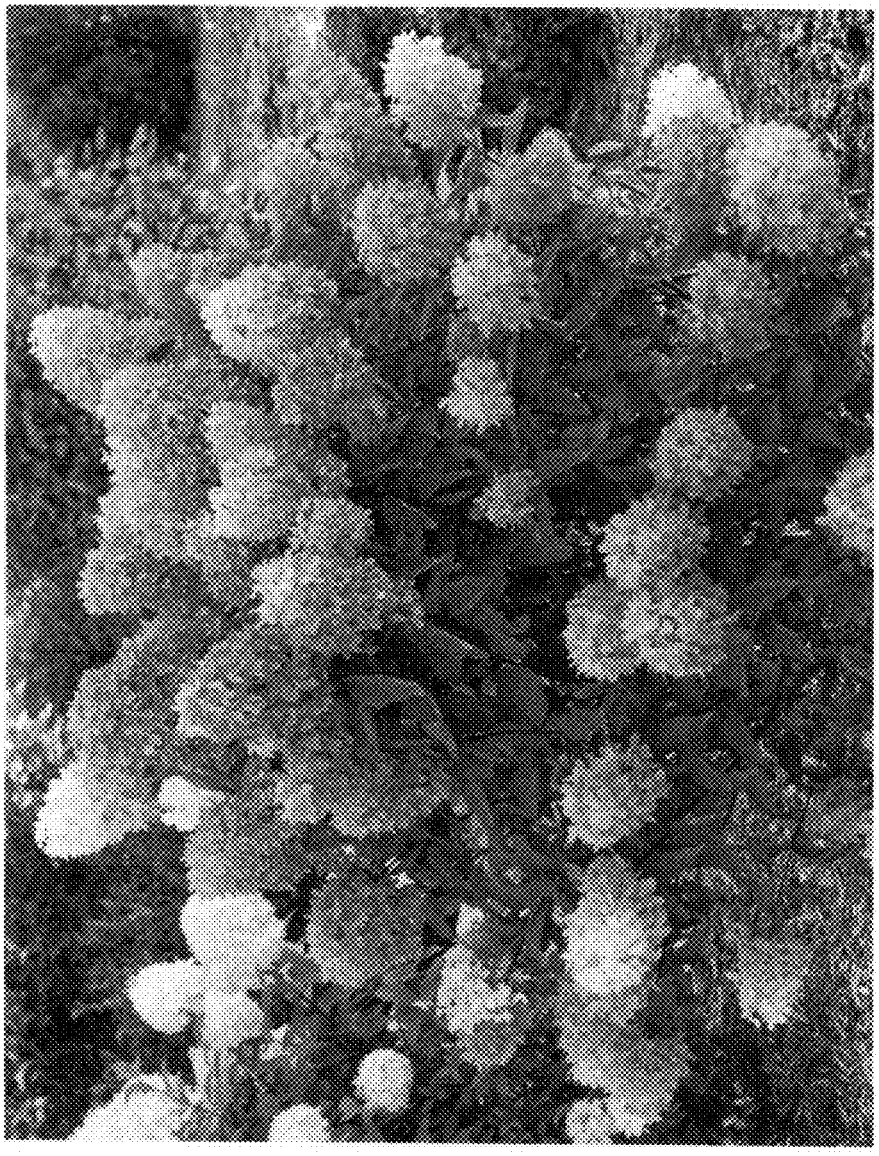

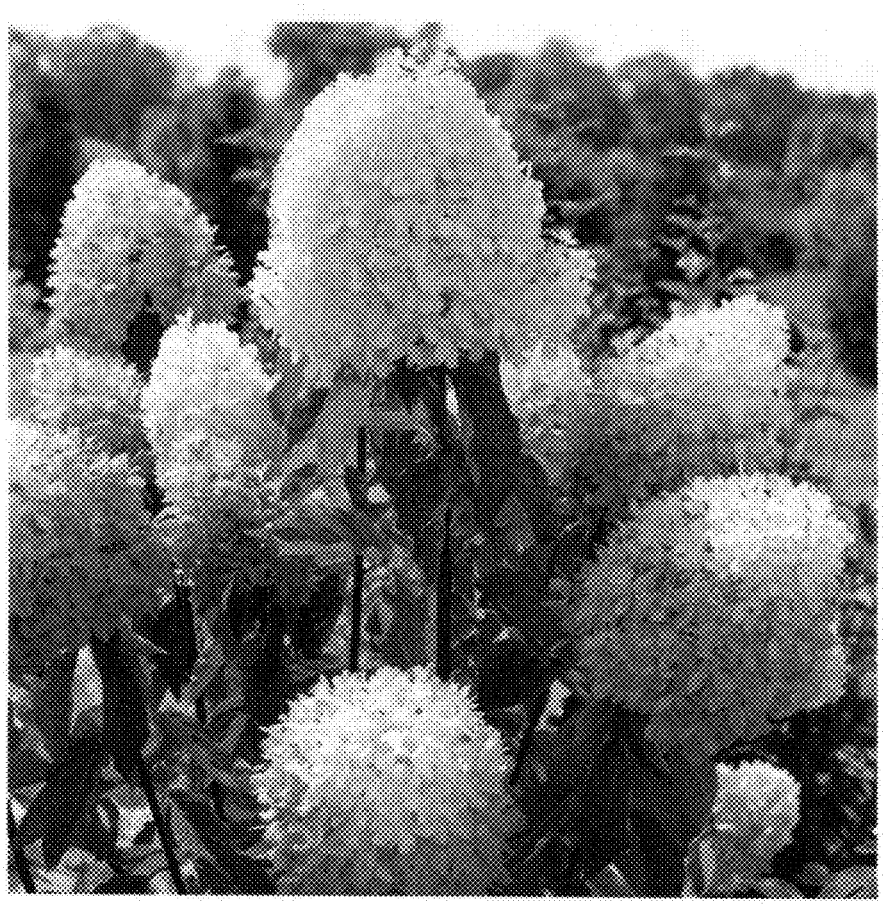

* * * * *